United States Patent
Kremer et al.

(10) Patent No.: US 11,282,492 B2
(45) Date of Patent: Mar. 22, 2022

(54) SMART-SAFE MASKING AND ALERTING SYSTEM

(71) Applicant: BOSE CORPORATION, Framingham, MA (US)

(72) Inventors: Kathleen Elizabeth Kremer, Southborough, MA (US); Jeffrey M. Ellenbogen, Towson, MD (US); Matthew Chace Carpenter, North Attleboro, MA (US); Steven Carl Pletcher, Hopkinton, MA (US); Chia-Ling Li, Framingham, MA (US)

(73) Assignee: BOSE CORPORATION, Framingham, MA (US)

( * ) Notice: Subject to any disclaimer, the term of this patent is extended or adjusted under 35 U.S.C. 154(b) by 90 days.

(21) Appl. No.: 16/278,380

(22) Filed: Feb. 18, 2019

(65) Prior Publication Data

US 2020/0265824 A1    Aug. 20, 2020

(51) Int. Cl.
    *G10K 11/175*    (2006.01)
    *A61M 21/02*    (2006.01)
    (Continued)

(52) U.S. Cl.
    CPC ........... *G10K 11/175* (2013.01); *A61M 21/02* (2013.01); *G08B 6/00* (2013.01); *G08B 7/06* (2013.01);
    (Continued)

(58) Field of Classification Search
    CPC .......... A61M 21/02; A61M 2205/3303; A61M 2205/3375; A61M 2205/581;
    (Continued)

(56) References Cited

U.S. PATENT DOCUMENTS

| 5,444,786 A | 8/1995 | Raviv |
| 9,087,447 B2 * | 7/2015 | Gruber .................. G08B 25/14 |

(Continued)

FOREIGN PATENT DOCUMENTS

| EP | 1 886 707 A1 | 2/2008 |
| WO | 2020086169 A2 | 4/2020 |

OTHER PUBLICATIONS

International Search Report and Written Opinion for International Application No. PCT/US2020/018337 dated Jun. 9, 2020, 12 pp.
(Continued)

*Primary Examiner* — Duc Nguyen
*Assistant Examiner* — Alexander L Eljaiek
(74) *Attorney, Agent, or Firm* — Patterson + Sheridan, LLP (57) ABSTRACT

Aspects of the present disclosure provide methods, apparatuses, and systems for a personalized wake-up system. A sleep assistance device outputs a sound. In response to detecting a sound that exhibits one or more predetermined sound properties, actions are taken to adjusting the sound in an effort to wake the subject. Examples of predetermined sound properties include any sound detected over a threshold decibel level, sounds detected at a certain frequency spectrum. According to aspects, subject may further configure the system to alert the subject based on a set of personalized sounds the subjects considers to be important. According to aspects, the audio device or system is configured to determine the subject is awake based on collected biosignal parameters. The audio device or system takes further actions to disrupt the subject's sleep until the subject is determined to be awake.

23 Claims, 4 Drawing Sheets (51) Int. Cl.
  *G08B 6/00* (2006.01)
  *G08B 7/06* (2006.01)
  *H04R 29/00* (2006.01)
  *A61M 21/00* (2006.01)
  *H04B 1/38* (2015.01)

(52) U.S. Cl.
  CPC ... *H04R 29/001* (2013.01); *A61M 2021/0027* (2013.01); *A61M 2205/3306* (2013.01); *A61M 2205/3375* (2013.01); *A61M 2205/3592* (2013.01); *A61M 2205/50* (2013.01); *A61M 2230/04* (2013.01); *A61M 2230/10* (2013.01); *A61M 2230/14* (2013.01); *A61M 2230/60* (2013.01); *A61M 2230/63* (2013.01); *H04B 1/38* (2013.01)

(58) Field of Classification Search
  CPC .... A61M 2205/583; A61M 2021/0022; G10K 11/175; G10K 11/178; G10K 2210/1081; G10K 2210/3028; G10K 2210/111; G10K 2210/3011; G10K 2210/3014; G10K 2210/509; H04R 1/1083; H04R 2420/07; H04R 2420/01; H04R 5/04; H04R 2430/01; H04R 2460/01; H04R 29/00; H04R 3/00; G06F 3/165; G06F 16/636; H03G 3/32; H03G 7/002; H04S 2400/13; H04W 4/38
  USPC ..... 340/575; 381/57, 71.6, 73.1, 74; 600/26, 600/28, 27; 700/94; 704/235
  See application file for complete search history.

(56) References Cited

U.S. PATENT DOCUMENTS

| | | | |
|---|---|---|---|
| 9,191,744 B2* | 11/2015 | Anderson | H04R 5/04 |
| 9,579,060 B1* | 2/2017 | Lisy | A61B 5/6803 |
| 10,791,986 B1 | 10/2020 | Kahn et al. | |
| 2004/0234080 A1 | 11/2004 | Hernandez et al. | |
| 2007/0173730 A1 | 7/2007 | Bikko | |
| 2008/0097764 A1 | 4/2008 | Grill et al. | |
| 2008/0243014 A1 | 10/2008 | Moussavi et al. | |
| 2009/0147965 A1 | 6/2009 | Kuo | |
| 2010/0258123 A1 | 10/2010 | Somaiya et al. | |
| 2010/0283618 A1 | 11/2010 | Wolfe et al. | |
| 2011/0295083 A1 | 12/2011 | Doelling et al. | |
| 2014/0051938 A1 | 2/2014 | Goldstein et al. | |
| 2015/0194144 A1* | 7/2015 | Park | H04K 3/41 381/73.1 |
| 2015/0258301 A1 | 9/2015 | Trivedi et al. | |
| 2015/0281829 A1 | 10/2015 | Gauger, Jr. et al. | |
| 2015/0294662 A1 | 10/2015 | Ibrahim | |
| 2015/0320588 A1 | 11/2015 | Connor | |
| 2016/0015315 A1 | 1/2016 | Auphan et al. | |
| 2016/0217672 A1 | 7/2016 | Yoon et al. | |
| 2017/0051551 A1 | 2/2017 | Smart | |
| 2017/0281119 A1* | 10/2017 | Stroman | A61B 5/002 |
| 2017/0319817 A1 | 11/2017 | Morishima et al. | |
| 2017/0323630 A1 | 11/2017 | Stickney et al. | |
| 2018/0078732 A1 | 3/2018 | Keshavan et al. | |
| 2018/0078733 A1 | 3/2018 | Freed et al. | |
| 2018/0078735 A1 | 3/2018 | Dalgleish et al. | |
| 2018/0082550 A1 | 3/2018 | Read et al. | |
| 2018/0236191 A1 | 8/2018 | Martin et al. | |
| 2019/0029563 A1 | 1/2019 | Sels et al. | |
| 2019/0030278 A1 | 1/2019 | Kremer et al. | |
| 2019/0046794 A1 | 2/2019 | Goodall et al. | |
| 2019/0073990 A1 | 3/2019 | Moss et al. | |
| 2019/0099009 A1 | 4/2019 | Connor | |
| 2020/0086076 A1 | 3/2020 | Mcelhone et al. | |
| 2020/0160828 A1 | 5/2020 | Taki et al. | |

OTHER PUBLICATIONS

International Search Report and Written Opinion for International Application No. PCT/US2020/018479 dated Jun. 16, 2020, 14 pp.
International Search Report and Written Opinion for International Application No. PCT/US2020/018483, dated Jun. 9, 2020, 12 pp.

* cited by examiner

SMART-SAFE MASKING AND ALERTING SYSTEM

FIELD

Aspects of the present disclosure generally relate to adjusting a sound in response to determining a detected sound exhibits one or more predetermined sound qualities. More particularly, aspects adjust a masking sound in an effort to allow a subject to hear sounds of importance.

BACKGROUND

Disruptions to a subject's sleep may result in poor sleep which negatively affects the subject's health. Sleep disruptions may be caused by environmental or ambient noises in the subject's sleeping environment that interrupt the subject's sleep. To try to block or compensate for such noises, a masking sound may be output in the subject's sleeping environment.

Masking sounds may help protect the subject's sleep; however, it may cover up the perception of sounds of importance in the subject's environment. Therefore, out of concern for missing important sounds, certain subjects may avoid use of sleep assistance devices. While a sleep assistance device of any kind (masking or otherwise) may help improve the subject's sleep, a need exists for a sleep protection device or system that both helps a subject sleep and allows certain sounds to be heard or perceived by the sleeping subject to awaken them.

SUMMARY

All examples and features mentioned herein can be combined in any technically possible manner.

According to aspects, an audio device or system is configured to output a sound, detect one or more sounds of importance in a sleeping environment, and take action to alert the subject of the detected sounds. Such actions used to enhance the subject's ability to hear the sounds of importance may include ceasing the masking sound, introducing an alert, or both.

In an aspect, the sounds may be output to protect the subject's sleep from noise-induced sleep disruption. Further, in aspects, one or more sounds of importance are detected in a sleeping environment to potentially take action if that sound is of significance to the sleep (e.g., fire alarm). Actions to enhance the sleeper's ability to hear the important sound can include ceasing masking sound, or introducing an alert, or both, to alert the subject of the detected sounds.

As will be described in more detail herein, in aspects, the audio device or system is configured to monitor biosignal parameters of the subject in an effort to confirm the subject is awake. According to aspects, the audio device or system is customized to monitor a combination of sounds having predetermined sound properties and sounds input by the subject. Accordingly, the method described herein provides a personalized sleep assistance experience for subjects while taking active steps to ensure the perception of sounds of importance are not covered up.

In one aspect, an audio device comprises a speaker configured to output a masking sound, at least one microphone configured to detect one or more sounds in a sleeping environment, and a processing unit. The processing unit is configured to determine whether the detected sound exhibits one or more predetermined sound properties, and, if so, adjust the masking sound to alert a subject of the one or more sounds while the subject is wearing the audio device in the sleeping environment. The speaker is further configured to output the adjusted masking sound.

The processing unit may be further configured to amplifying an intensity of the detected one or more sounds, and the speaker may be further configured to output the amplified detected one or more sounds. The processing unit may be configured to adjust the masking sound by reducing a sound intensity of the masking sound. The processing unit may be further configured to introduce at least one haptic output to alert the subject of the one or more sounds while the subject is wearing the audio device in the sleep environment. The processing unit may be further configured to introduce at least one visual cue to alert the subject of the one or more sounds while the subject is wearing the audio device in the sleep environment, and may further comprise a transceiver configured to wirelessly transmit a command to introduce the visual cue in the sleeping environment.

The audio device may further comprise a transceiver configured to wirelessly detect the one or more sounds. The audio device may further comprise at least one biosensor configured to measure at least one biosignal parameter of the subject while the subject is wearing the wearable audio device and the speaker is outputting the adjusted masking sound, and the processing unit may be further configured to determine the subject is sleeping based on the biosignal parameter, and in response to determining the subject is sleeping, performing at least one of: further decreasing an intensity of the adjusted masking sound, introducing haptics, amplifying an intensity of the detected one or more sounds, or wirelessly transmitting, via a transceiver, a command to introduce a visual cue in the sleep environment in an effort to alert the subject of the one or more sounds.

The audio device may further comprise transceiver configured to wirelessly receive input from the subject indicating at least one of the one or more sounds. The one or more predetermined sound properties may comprise noise over a predetermined decibel level. The one or more predetermined sound properties may comprise noise over a predetermined decibel level within a predetermined frequency spectrum.

In another aspect, a method for alerting a subject comprises outputting a masking sound, detecting one or more sounds in a vicinity of the subject, determining whether the detected sound exhibits one or more predetermined sound properties, and in response to determining that the detected sound exhibits the one or more predetermined sound properties, adjusting the masking sound to alert the subject of the one or more detected sounds. The method further comprises outputting the adjusted masking sound, detecting a biosignal parameter of the subject while outputting the adjusted masking sound, determining, based at least in part on the detected biosignal parameter, the subject is sleeping, and further adjusting the adjusted masking sound in an effort to alert the subject of the detected one or more sounds.

Adjusting the masking sound may comprises at least one of: reducing a sound pressure level of the masking sound or altering a frequency spectrum of the masking sound. The method may further comprise in response to determining the subject is sleeping, introducing at least one of a visual cue or haptic output in an effort to alert the subject of the detected one or more sounds, monitoring the biosignal parameter of the subject while introducing the visual cue or haptic output, determining the subject is not awake based on the monitored biosignal parameter, and in response to determining the subject is not awake, continuing the visual cue or the haptic output.

The method may further comprise determining the subject is awake based on the monitored biosignal parameter, and in response to determining the subject is awake, stopping the visual cue or the haptic output. The method may further comprise in response to determining the subject is sleeping, gradually increasing a sound pressure level of the masking sound until the subject is determined to be awake. The subject may be determined to be awake based on a determined biosignal parameter. The subject may be determined to be awake based on input received from the subject.

The one or more sounds may comprise a combination of preconfigured safety alarms and sounds selected by the subject. At least one of the sounds selected by the subject may comprise a sound recorded by the subject. Detecting the one or more sounds in the vicinity of the subject may comprise wirelessly receiving an indication of the detected one or more sounds.

In yet another aspect, a wearable audio device comprises a speaker configured to output a masking sound at a first sound pressure level (SPL), at least one microphone configured to detect a noise greater than a threshold decibel value in a sleeping environment, and a processing unit configured to decrease the masking sound from the first SPL to a second SPL, in an effort to alert a subject of the detected noise while the subject is wearing the audio device in the sleeping environment. The speaker is further configured to output the masking sound at the second SPL. The wearable audio device further comprises a biosensor configured to detect a biosignal parameter of the subject while the subject is wearing the wearable audio device and the speaker is outputting the masking sound at the second SPL. The processing unit is configured to determine the subject is not awake based on the biosignal parameter, and in response to the determination, wirelessly introduce a visual cue or a haptic output until the subject is determined to be awake based on a detected biosignal parameter.

The processing unit may be further configured to amplify the detected noise in response to determining the subject is not awake.

Advantages of alerting a subject by adjusting a masking sound in response to a detected sound exhibiting one or more predetermined sound properties will be apparent from the description and the claims.

DETAILED DESCRIPTION

A sleep assistance or sleep protection device outputs masking sounds to help subjects fall and stay asleep. A limitation to exposing a subject to masking sound while sleeping is that the subject may not hear sounds of importance. Based on the subject-selected volume of a mask, certain sleep assistance devices provide a warning indicating that the subject may not be able to hear sounds of importance. Sounds of importance include fire alarms, home safety alarms, telephone calls from certain people, or any other alarms, alerts, or noises the subject desires to hear or should hear for safety reasons. Sounds of importance may be customized by a subject to include subject-specific sounds of importance, such as a baby crying. Currently, some subjects avoid use of sleep assistance devices because they fear sleeping through sounds of importance. Others set a volume of masking output by the sleep assistance device to be so low that the masking is not effective at protecting sleep.

In an effort to address this limitation while still providing the benefits of a sleep assistance device, aspects describe methods, apparatus, and systems for outputting a masking sound, identifying sounds in a subject's sleeping environment, determining if the sounds exhibits one or more predetermined sound properties, and, if so, adjusting a masking sound. As described below, adjusting the masking sound includes any combination of reducing the sound pressure level of a mask, refraining from masking, altering a spectral content of a mask, introducing and outputting a new alert, or notching the detected sound exhibiting the predetermined sound properties so the frequency of the sound of importance passes through a notch filter. According to aspects, the methods, apparatus, and systems are further configured to monitor a biosignal parameter in an effort to determine if the subject is still sleeping. When the subject is determined not to be awake, the audio device or system takes further action in an attempt to wake the subject. The apparatus may include an audio device, a wearable, or a bedside unit. A system may include any combination of apparatuses wherein one or more of the apparatuses may communicate with sensors or alarms in a subject's sleep environment. While the term "masking sound" is used throughout, the described methods, apparatus, and systems are not limited to only masking sounds, and the term "masking sound" as used herein includes other such sounds to be played in a sleeping environment, such as soothing sounds, audio therapeutics, relaxation soundtracks, entrainment soundtracks, etc.

Figure 1:
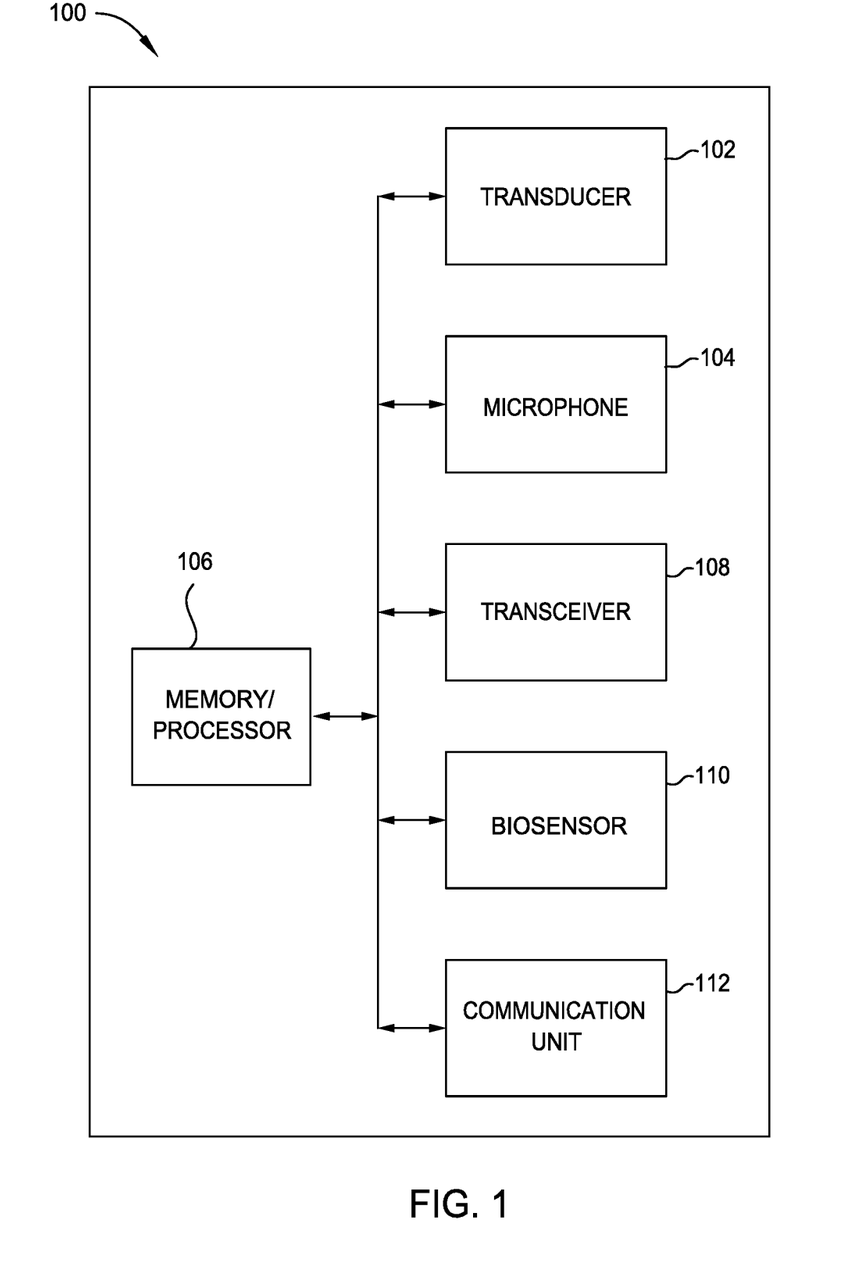
FIG. 1 illustrates example components of an audio device.

FIG. 1 illustrates example components of an audio device 100, in accordance with certain aspects of the present disclosure. In an example, the audio device is a headphone that fits around, on, or in an ear and that radiates acoustic energy into the ear canal. Headphones may be referred to as earphones, earpieces, headsets, earbuds, or sport headphones, and can be wired or wireless. In an aspect, the audio device 100 is configured to perform active noise reduction (ANR). Any or all of the components in FIG. 1 may be combined into multi-function components.

In one example, the audio device 100 includes an audio output transducer or speaker 102, a microphone 104, and a memory and processor 106. The audio device 100 optionally includes a transceiver 108, a biosensor 110, and a communication unit 112.

The audio output transducer 102 may be also known as a driver or speaker. In some examples, more than one output transducer is used. The transducer converts electrical signals into sound and converts sound into electrical signals. The speaker is configured to output a masking sound. Further, the speaker is configured to output the adjusted masking sound based on determining a detected sound exhibits one or more predetermined sound properties. While the term "masking sound" is used throughout, the speaker is not limited to outputting and adjusting only masking sounds. The term "masking sound" as used herein includes other such sounds to be played in a sleeping environment, such as soothing sounds, audio therapeutics, relaxation soundtracks, entrainment soundtracks, etc.

The microphone 104 is configured to detect the sounds in the subject's sleeping environment. The microphone is configured to convert the detected noise into electrical signals. The terms "noise" and "sound" are used interchangeably in this document.

The memory and processor (processing unit) 106 control the operations of the audio device 100. The memory stores program code for controlling the memory and processor 106. The memory may include Read Only Memory (ROM), a Random Access Memory (RAM), and/or a flash ROM.

The processor 106 controls the general operation of the audio device 100. The processor 106 performs process and control for audio and/or data communication. In addition to the general operation, the processor 106 is configured to determine whether a sound detected by the microphone is a sound of importance to the subject. Sounds of importance exhibit a certain sound property such as exceeding a threshold decibel level, occupying a specific frequency spectrum, or being specific to a subject. Example sounds of importance include alarms, alerts, and other safety notifications.

Sounds of importance may be personal to the subject. In an example, co-parents may split nighttime care responsibilities of a baby. A subject may wish to hear a crying baby one night and the subject may wish to sleep though crying noises another night, such as when a co-parent is assuming primary caregiving responsibilities. In another example, a pilot may use a masking device to block certain noises in an airplane; however, the pilot may wish to always hear certain alarms and sounds. In another example, two co-pilots alternate flying responsibilities and each may use a masking device to block noises on board the flight. When off-duty, a co-pilot may wish to hear certain emergency alarms only and the on-duty co-pilot may wish to hear more alerts than just emergency alarms. Each co-pilot is able to select sounds of importance. Stated otherwise, each co-pilot is able to choose, in general or per situation, certain sounds to be blocked and certain sounds to be unblocked.

If a detected sound is determined to be a sound of importance, the processor is configured to adjust a masking sound to alert the subject of the detected sound of importance. Adjusting the masking sound may comprise stopping the masking sound from being output and introducing an alerting sound. In aspects, adjusting a masking sound includes reducing a sound pressure level of the masking sound and adjusting a spectral content of the mask. According to aspects, the processor 106 is further configured to introduce at least one haptic output and/or visual cue.

In aspects, the audio device includes a communication unit 112 that facilitates a wireless connection with one or more other devices. For example, the communication unit 112 may include one or more wireless protocol engines such as a Bluetooth engine. While Bluetooth is used as an example protocol, other communication protocols may also be used. Some examples include Bluetooth Low Energy (BLE), Near Field Communications (NFC), IEEE 802.11, or other local area network (LAN) or personal area network (PAN) protocols.

In aspects, the communication unit 112 wirelessly communicates with a handheld device such as a tablet or cell phone. In an example, an application executed on the audio device or an external handheld device presents a list of potentially important sounds. The subject selects which of the sounds are important. Example sounds include crying baby, dishwasher noises, loud bang, door bell, and car alarm. For safety reasons, certain sounds, such as fire alarms, are preconfigured to be sounds of importance. The subject may further select one or more sounds to block. In aspects, a subject records sound of importance. In an example, the subject records a crying baby or other specific sounds the subject would like to hear. The processor 106 is configured to match sounds detected by the microphone with the previously-recorded sound to identify sounds of importance.

In an example, the subject wearing the audio device 100 experiences a sleep disruption. The subject inputs information indicating the time or an approximate time the subject woke up at certain times during a sleeping period in an application on a handheld device. The processor 106 correlates the time of subject-entered sleep disruption with sounds in the sleeping environment to learn which sounds disturbed the subject. An application executed on the audio device or a separate handheld device may include sounds determined to have disrupted a subject's sleep in the set of sounds from which the subject selects sounds of importance.

In an aspect, the communication unit 112 receives information associated with a subject's biosignal parameters, obtained via a contactless sensor. Examples of contactless sensors include a radio frequency (RF) sensor or an under-bed accelerometer.

In aspects, a transceiver 108 transmits and receives information via one or more antennae to exchange information with one or more other devices. The one or more other devices include the devices illustrated in FIG. 2 as well as sensors and microphones that are distributed throughout a subject's sleeping environment 200, 300. The transceiver 108 is not necessarily a distinct component. The transceiver 108 is configured to transmit and receive information from an application running on an external wireless device, such as a handheld device. According to aspects, the transceiver 108 in combination with the communication unit 112 communicates with the internet, networks, or hub services such as the cloud.

According to aspects, a biosensor 110 is configured to sense or calculate a biosignal parameter of a subject wearing the audio device 100. According to an example, the biosensor 110 is one of a photoplethysmography (PPG) sensor, electroencephalogram (EEG) sensor, electrocardiogram (ECG) sensor, electrooculogram (EOG) sensor, electromyogram (EMG) sensor, accelerometer, a microphone, or other suitable devices. The biosensor 110 may be any sensor configured to determine, sense, or calculate a subject's biosignal parameter. In one example, the biosensor 110 is located on an ear tip of at least one earpiece, thereby contacting the subject's skin when inserted in the subject's ear.

In an example, the biosensor 110 is configured to determine if the subject is awake or asleep. In an example, the subject's biosignal parameter, or values of a biosignal parameter over a period of time, is compared to benchmark biosignal parameters to determine if the subject is awake. Benchmarks may be associated with collected parameters from a subset of the population. In aspects, the benchmarks are specific to a gender, age range, or combination of gender and age range. Based on the subject's gender and age, the audio device compares the subject's collected biosignal parameters with the benchmark data to determine if the subject is awake. As described below, after outputting the adjusted masking sound, the audio device is further configured to determine if the subject is awake based on the biosignal parameter. If the subject is determined not to be awake, then audio device may further reduce the mask or adjust a spectral content of the mask in an effort to alert the subject of the sound of importance. In aspects, if the subject is determined not to be awake, the audio device may additionally or alternatively introduce one or more other outputs such as haptic outputs or visual cues in an effort to wake the subject.

FIG. 1 illustrates communication between certain modules of an example open audio device; however, aspects of the disclosure are not limited to the specific illustrated example. According to aspects, any module 102-112 is configured to communicate with any other module in the audio device. In one example, all modules are connected to and communicate with each other.

According to aspects, the audio device 100 includes fewer components than illustrated in FIG. 1. In one example, the audio device may not include a biosensor or a communication unit. Even without certain components, the audio device is configured to output a masking sound, identify sounds of importance, and adjust the masking sound in an effort to alert a subject.

Figure 2:
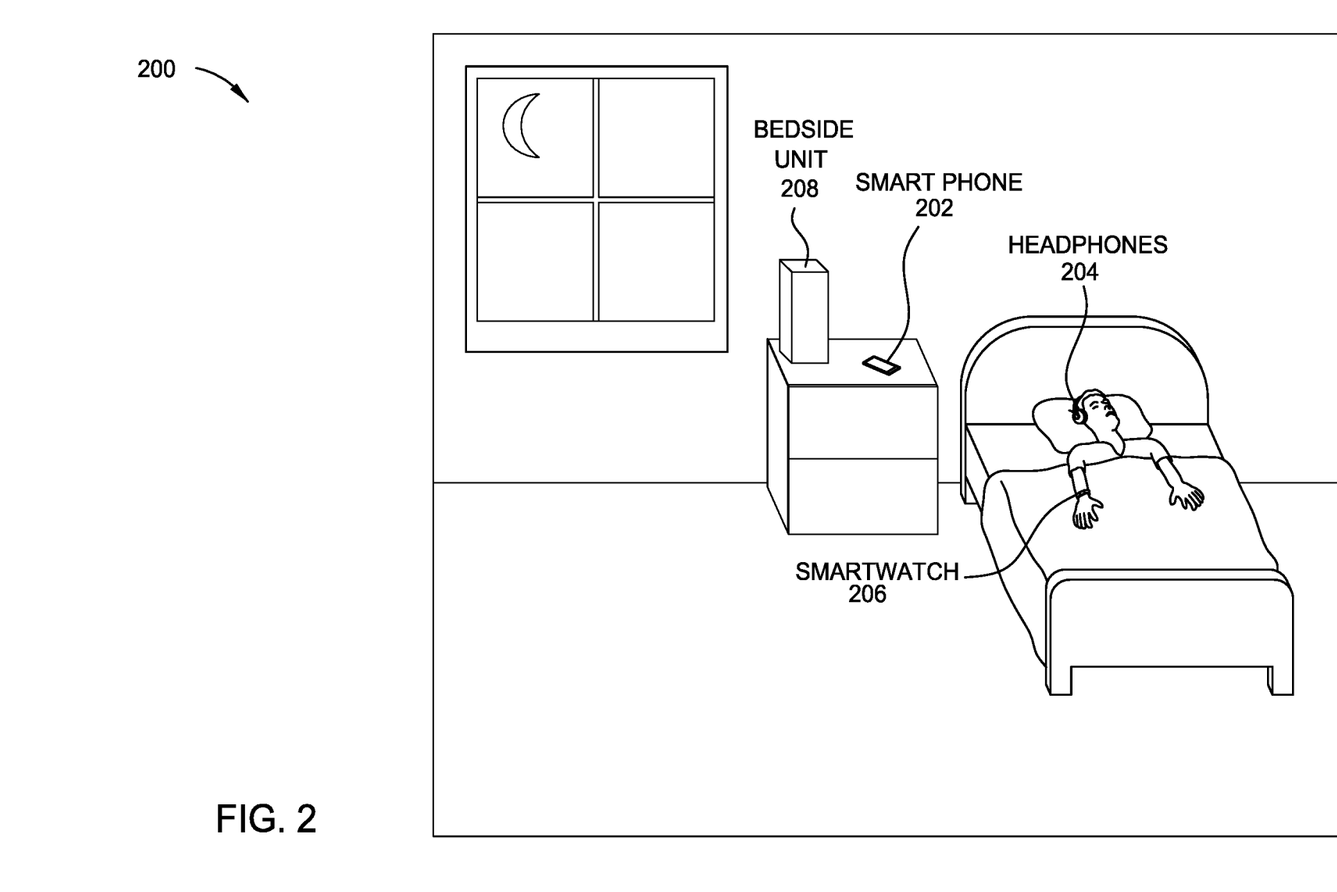
FIG. 2 illustrates an example system in an example sleep environment.

FIG. 2 illustrates an example system 200 in a sleeping environment, according to aspects of the present disclosure. The audio system 200 outputs masking sounds and takes action to alert a subject of identified sounds of importance by outputting an adjusted masking sound. While the term "masking sound" is used throughout, the audio system 200 is not limited to outputting and adjusting only masking sounds. The term "masking sound" as used herein includes other such sounds to be played in a sleeping environment, such as soothing sounds, audio therapeutics, relaxation soundtracks, entrainment soundtracks, etc. In an example, the audio system 200 includes one or more of an audio device 204, a smartwatch 206, a smartphone 202, and a bedside unit 208.

The audio device 204 may be the audio device 100 illustrated in FIG. 1. A smartwatch 206 may be any type of wearable computer designed to be worn on a wrist of a subject, such as a fitness tracker. The smartphone 202 may be a mobile phone, tablet, phablet, or laptop computer. The bedside unit 208 may be a stationary smart device, such as a smart speaker. The bedside unit 208 may have any shape and size capable of fitting on a surface in the sleeping environment, such as a dresser, desk, or night table.

The smartwatch 206, smartphone 202, and bedside unit 208 may include any combination of the components illustrated in the audio device of FIG. 1. In an example, the audio device 204, smartwatch 206, bedside unit 208, and smartphone 202 may each include any wired or wireless communication means suitable for use with any other device 202-208 disposed in the sleeping environment. Thus, each device 202-208 in the audio system 200 may be optionally included in a system configured to adjust masking sound to alert a subject of a detected sound of importance, and only one of the devices 202-208 is needed to output a masking sound and alert the subject of a sound of importance.

In an example, the audio device 204 comprises one or more speakers configured to output the masking sound and output the adjusted masking sound, and the bedside unit 208 comprises one or more microphones in communication with the one or more speakers of the audio device 204. The microphones on the bedside unit 208 are configured to detect sounds in the subject's sleeping environment.

Figure 3:
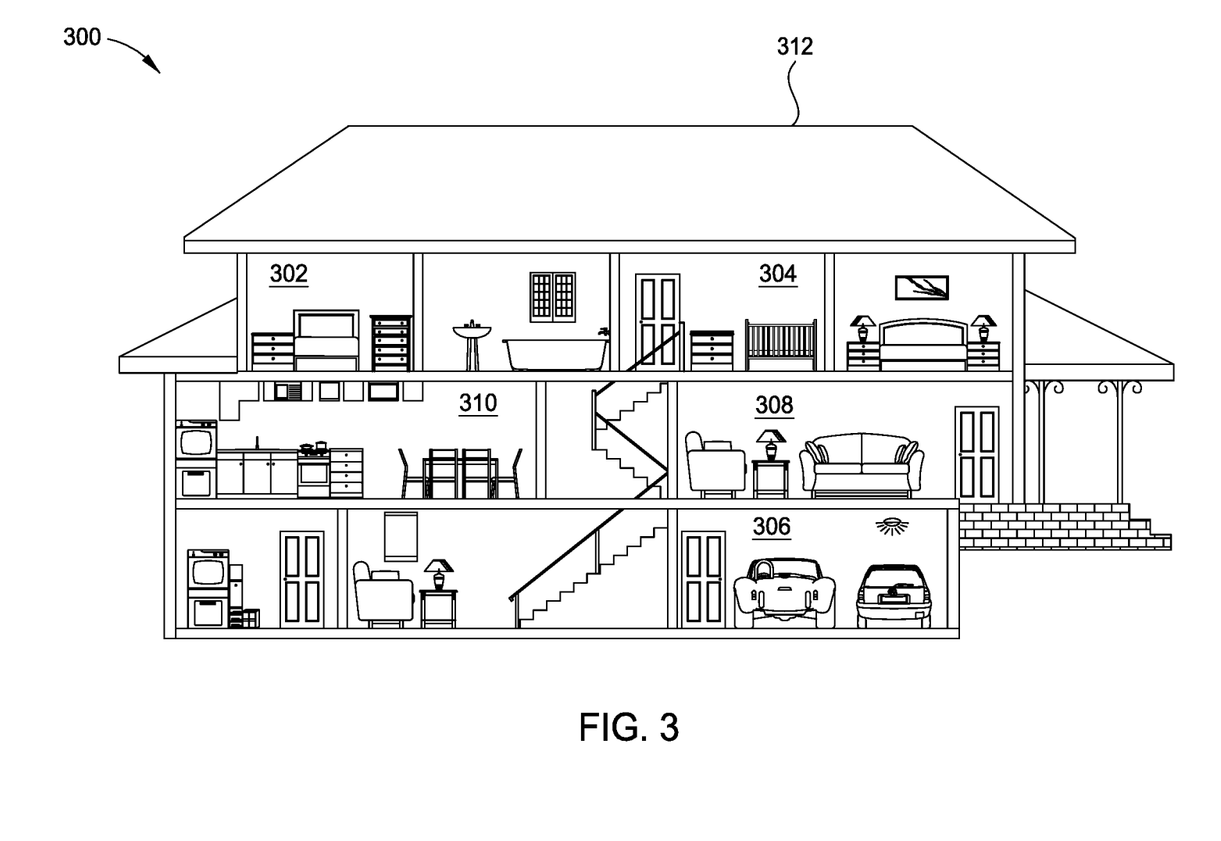
FIG. 3 illustrates an example of a sleep environment that may include the sleep environment illustrated in FIG. 2.

FIG. 3 illustrates an example sleep environment 300. The sleep environment 300 may be a bedroom 302 illustrated in FIG. 3. A sleep environment includes not only the sleeping subject's immediate surroundings including the subject's bedroom 302, but also other rooms in the house 312. In an example integrated house scenario, microphones, detectors, sensors, or alarms are distributed throughout rooms or areas of the house 312. One or more devices illustrated in FIG. 2 are configured to receive wireless indications of detected sounds from the distributed microphones, detectors, sensors, or alarms. In a non-integrated house scenario, one or more devices illustrated in FIG. 2 are wired such that microphones, detectors, sensors, or alarms throughout the house 312 are tied to the one or more devices.

According to aspects, the sound may not originate in the subject's immediate sleeping environment; however, the sound may still exhibit certain sound properties indicative of a sound the subject should hear. As an example, a fire alarm in a garage 306 may exceed a threshold decibel value in the garage; however, a subject sleeping in a bedroom 302 may not be able to hear the alarm. As described herein, microphones in the garage may transmit an indication of the detected sounds to the audio device 100, 204 or any device in system 200. The audio device may receive, via the transceiver 108, an indication of the detected sound and the processor 106 adjusts the mask for a subject sleeping in a bedroom 302 based on the detected sound of importance in the garage 306.

Sounds of importance are either preconfigured or selected by a subject. In one example, sounds of importance are any sound that exceeds a threshold decibel value, occupies a particular frequency spectrum, or both exceeds a threshold decibel value and occupies a particular frequency spectrum. For illustrative purposes, a fire alarm goes off in the garage 306 and a foreign object shatters a window in the living room 308 triggering a home security alarm. According to aspects, the fire alarm and home security alarm are output at a decibel level exceeding a threshold value. Therefore, even if the subject did not manually select these sounds as sounds of importance, the audio device or system described herein would adjust a mask in an effort to alert the subject.

In an example, sounds of importance are selected by the subject. According to aspects, the subject selects sounds of importance from a set of sounds. In aspects, the subject records actual sounds and uploads them to an application. The uploaded sounds may be selected as a sound of importance. In one example, sounds of a crying baby are identified as a sound of personalized importance. A baby monitor in a nursery 304 detects sounds of a crying baby which triggers a device, perhaps in the subject's bedroom 302, to adjust a mask and output the adjusted mask. Additionally, a subject may select sounds to be blocked.

Figure 4:
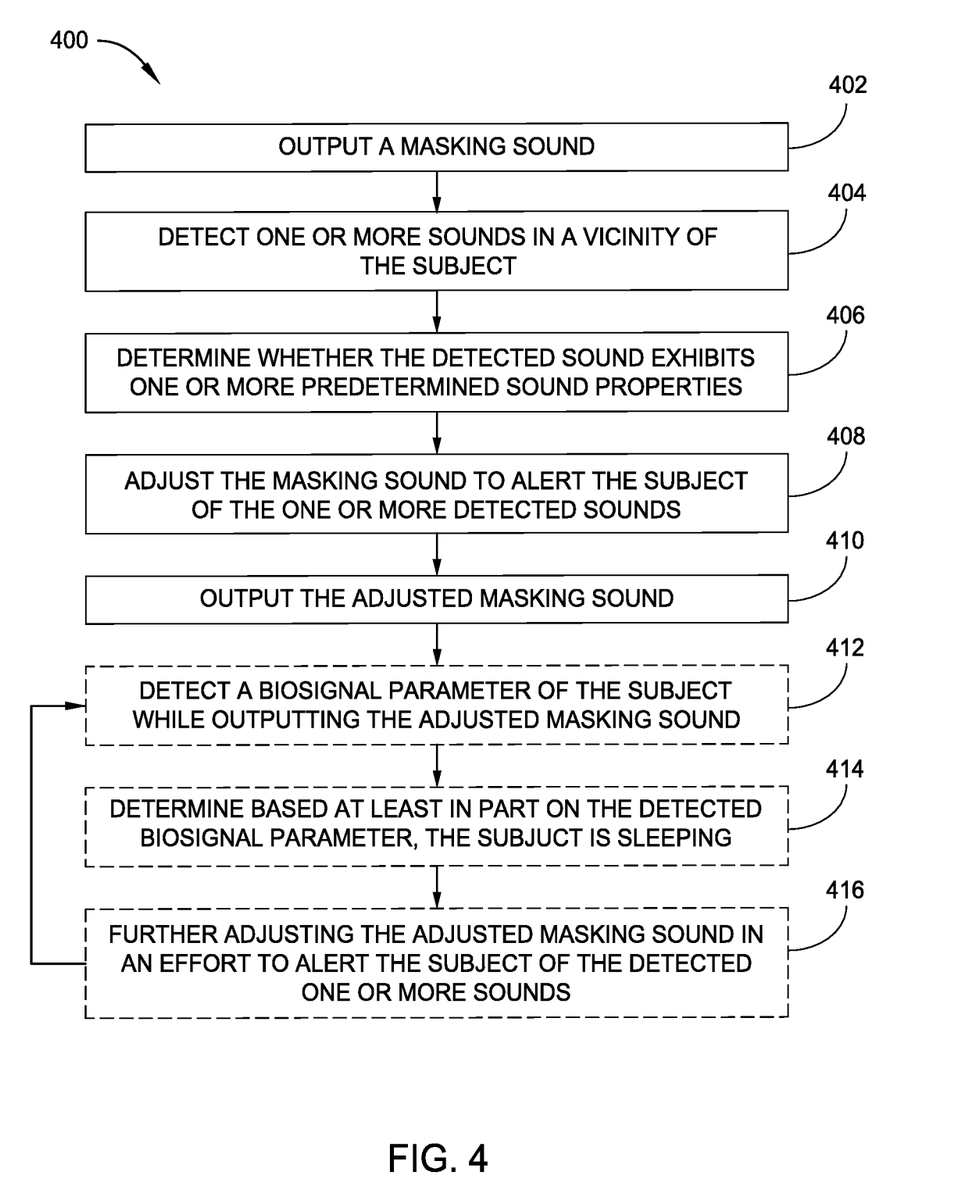
FIG. 4 illustrates an example method adjusting a mask to alert a subject of sounds of importance that may be performed by an audio device or a system of devices.

FIG. 4 illustrates example operations 400 for alerting a subject of a sound of importance. The operations 400 may be performed by the audio device 100, 204. In one example, the audio device 100, 204 that performs the operations 400 does not include a biosensor or a communication unit. According to aspects, one or more components of an audio system 200 are configured to perform the operations 400.

At 402, a masking sound is output. A masking sound may be a soundscape or shaped noise which attempts to help subjects fall and stay asleep. The sound may be output by the audio device, a wearable device, a bedside unit, or speakers positioned in the subject's sleep environment.

At 404, at least one microphone detects one or more sounds in a vicinity of the subject. The vicinity of the subject may refer to the subject's sleeping environment which includes the room in which the subject is sleeping and areas surrounding the room. As shown in FIG. 3, the sleeping environment may refer to not only the subject's bedroom 302, but also other rooms in the house 312 and the area surrounding the subject's house 300. According to aspects, rooms in the house 312 are integrated, wherein at least a subset of rooms, such as a subject's bedroom 302, nursery 304, garage 306, living room 308, and kitchen 310, are equipped with microphones and/or other sensors to detect noise or motion in the respective room that wirelessly communicate with a device in the system 200. In an example, one or more of the rooms in the house 312 include a microphone. When noise or motion is detected, an indication is transmitted to a transceiver of a device in the system 200. The transceiver communicates with a processing unit and speaker to adjust masking sounds and output the adjusted masking sounds.

At 406, at least one processor determines whether the detected sound exhibits one or more predetermined sound properties. The predetermined sound properties include the decibel level of the sound being greater than a configurable threshold decibel level, the sound matching a specific range of frequencies, the decibel level of the sound being greater than a configurable threshold decibel level over a range of frequencies, or the sound matching a customized sound that the subject identifies as a sound of importance. As noted above, a subject may record a sound of importance. Using an application on a smart device, the user may upload the recorded sound clip and the processor is configured to determine if a detected sound matches sound properties of the recorded sound. In aspects, the subject identifies noises which the subject considers sounds of importance. The subject identifies the noises from a set of options provided by an application running on a smart device. The subject can conveniently change which sounds are important based on user preferences to create a more personalized sleep product.

In response to determining a detected sound exhibiting predetermined sound properties, at 408, the masking sound is adjusted to alert the subject of the one or more detected sounds. Adjusting the masking sound may include stopping the masking sound from being output, or changing the masking sound to an alerting sound. At 410, the adjusted masking sound is output. According to aspects, the masking sound is adjusted by reducing a sound intensity of the masking sound. In aspects, a speaker stops outputting the masking sound completely and outputs an alerting sound. The alerting sound may be intended to wake a sleeping subject.

In aspects, in addition to adjusting and outputting adjusted masking sounds, a speaker is configured to amplify an intensity of the detected sounds of importance. According to aspects, the sound of importance is notched so the frequencies associated with the sound pass through a notch filter and the perception of the sound of importance is not covered up. According to aspects, a processor is configured to alert the subject of the sound of importance by introducing haptics or visual cues. In an example, an in-ear audio device is configured to vibrate in an effort to disrupt the subject's sleep. In an aspect, one or more lights in the subject's sleeping environment are configured to receive an indication of the sounds of interest and flash in an effort to alert the subject of the sounds of interest. According to aspects, a transceiver in one of the audio device or bedside unit is configured to wirelessly communicate with smart lights in the subject's sleeping environment. The adjusted masking sound, haptics, and visual cues are output until the subject turns them off, for example, using a feature of an application in communication with the audio device or system.

In certain aspects, steps 412-416 are performed to make sure the subject wakes up. At 412, a biosignal parameter of the subject is detected, sensed, or measured while the adjusted masking sound is output. Based on a collected biosignal parameter, the audio device determines if the subject is asleep or awake. In an example, the subject's biosignal parameter, or values of a biosignal parameter over a period of time, is compared to benchmark biosignal parameters to determine if the subject is awake or asleep. Benchmarks may be associated with collected parameters from a subset of the population. In aspects, the benchmarks are specific to a gender, age range, or combination of gender and age range. Based on the subject's gender and age, the audio device compares the subject's collected biosignal parameters with the benchmark data to determine if the subject is awake.

When, at 414, the subject is determined to be sleeping based on the biosignal parameter, the audio device at, 416, further adjusts the masking sound in an effort to alert the subject of the detected sounds exhibiting the one or more predetermined sound properties.

According to aspects, further adjusting the masking sound includes further decreasing the level of masking until the subject is determined to be awake. In an example, the sound pressure level of the mask gradually decreases so that the subject is more likely to hear the sound from the sleeping environment. The sound pressure level may decrease until the subject is determined to be awake. In aspects, further adjusting the mask includes dropping the sound pressure level of the mask to zero in an effort to quickly wake the subject. In aspects further adjusting the mask includes further altering the frequency spectrum of the mask in an effort to allow the sounds of importance to be heard more clearly by the subject. Further adjusting the masking sound may include increase a volume or frequency of the masking sound such that the masking sound is an alerting sound intended to wake a sleeping subject.

According to aspects, in response to determining the subject is still sleeping (at 414), the audio device is configured to introduce notifications to wake the subject. An example of a notification includes introducing haptics. In an example, a wearable or an ear tip of and audio device vibrates in an effort to disrupt the subject's sleep. Other example notifications include amplifying an intensity of the detected sound of interest, transmitting a command to introduce a visual cue in the subject's sleeping environment, or any combination of notifications described above. In aspects, one or more of these notifications are introduced until the subject is determined to be awake.

According to aspects, after further adjusting the masking sound, the method returns to 412, where biosignal parameters of the subject are monitored. According to aspects, if the subject is still determined to be asleep, additional notifications such as in-ear alarm, haptic output, or visual cues continue. The additional notifications stop once the subject is determined to be awake. The subject is determined to be awake based on a determined biosignal parameter or user input. In an example, a subject turns off a feature on a wearable device using an application to indicate the subject is awake.

In one exemplary embodiment, a masking sound is output to a subject (402). A microphone then detects one or more sounds in a vicinity of the subject (404). The processor then determines that the detected sound exhibits one or more predetermined sound properties (406). The masking sound is then adjusted and output, or refrained from being output completely (408 and 410). The audio device may adjust the masking sound by stopping the masking sound from being output and outputting an alerting sound intended to wake a sleeping subject. A biosignal parameter of the subject is detected, sensed, or measured while the adjusted masking sound is output (412). Based on the biosensor parameter, the subject is determined to be sleeping or unaware of that the detected sound exhibits one or more predetermined sound properties (414). The audio device then further adjusts the masking sound in an effort to alert the subject of the detected sounds exhibiting the one or more predetermined sound properties (416). Further adjusting the masking sound may include increase a volume or frequency of the masking sound to be an alerting sound.

FIGS. 2 and 3 illustrates example sleeping environments and FIG. 4 provides example operations for illustration purposes only. Aspects cover any method, device, or system capable of outputting a masking sound, detecting a sound of importance, and adjusting a mask in an effort to alert the subject of the detected sound of importance. Optionally, in certain aspects, the mask is further adjusted based on determining if the subject is still sleeping. In addition to adjusting or further adjusting the mask, other notifications such as haptics, visual cues, or introduction of audio alarms are output to alert the subject of the sound of importance. According to aspects, based on the sound of importance, the output by a device or system may be configured. For example, for a fire alarm, the user may configure a system to adjust a mask and output haptics. In this manner, subjects are quickly alerted to sounds of importance in a multi-modal fashion. The subject's ability to select sounds of importance helps to create a personalized sleep assistance device. The incorporation of biometric information ensures the subject is awake and creates a personalized closed-loop wake-up system.

According to aspects, the audio device or system described herein is also configured to predictively mask potentially distributing sounds prior to their occurrence as described in U.S. patent application Ser. No. 16/278,322 entitled "Dynamic Masking With Dynamic Parameters," filed on Feb. 18, 2019, which is hereby incorporated by reference in its entirety.

In the preceding, reference is made to aspects presented in this disclosure. However, the scope of the present disclosure is not limited to specific described aspects. Aspects of the present disclosure may take the form of an entirely hardware embodiment, an entirely software embodiment (including firmware, resident software, micro-code, etc.) or an embodiment combining software and hardware aspects that may all generally be referred to herein as a "component," "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples of a computer readable storage medium include: an electrical connection having one or more wires, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the current context, a computer readable storage medium may be any tangible medium that can contain, or store a program.

The flowchart and block diagrams in the Figures illustrate the architecture, functionality and operation of possible implementations of systems, methods and computer program products according to various aspects. In this regard, each block in the flowchart or block diagrams may represent a module, segment or portion of code, which comprises one or more executable instructions for implementing the specified logical function(s). In some implementations, the functions noted in the block may occur out of the order noted in the figures. For example, two blocks shown in succession may, in fact, be executed substantially concurrently, or the blocks may sometimes be executed in the reverse order, depending upon the functionality involved. Each block of the block diagrams and/or flowchart illustrations, and combinations of blocks in the block diagrams and/or flowchart illustrations can be implemented by special-purpose hardware-based systems that perform the specified functions or acts, or combinations of special purpose hardware and computer instructions.

The invention claimed is:

1. An audio device comprising:
a speaker configured to output a masking sound;
at least one microphone configured to detect one or more sounds in a sleeping environment, wherein the sleeping environment includes a plurality of rooms and wherein the at least one microphone is located in one of the plurality of rooms;
at least one alarm or detector distributed in a different one of the plurality of rooms than the one occupied by the at least one microphone; and
a processing unit configured to:
determine whether the one or more sounds detected by the at least one microphone exhibits one or more predetermined sound properties and satisfies criteria for a sound of importance upon processing the one or more sounds with a notch filter,
determine whether the at least one alarm or detector provides an indication of a different sound that exhibits the one or more predetermined sound properties, and satisfies the criteria for the sound of importance upon processing the different sound with the notch filter, and,
upon determining that either the one or more sounds or the different sound exhibits the one or more predetermined sound properties and satisfies the criteria for the sound of importance, adjust the masking sound to awake a subject in a closed-loop manner in response to the determination of the one or more sounds while the subject is wearing the audio device in the sleeping environment,
wherein the speaker is further configured to output the adjusted masking sound.

2. The audio device of claim 1, wherein:
the processing unit is further configured to amplify an intensity of the detected one or more sounds, and
the speaker is further configured to output the amplified detected one or more sounds.

3. The audio device of claim 1, wherein the processing unit is configured to adjust the masking sound by reducing a sound intensity of the masking sound.

4. The audio device or claim 1, wherein the processing unit is further configured to introduce at least one haptic output to alert the subject of the one or more sounds while the subject is wearing the audio device in the sleep environment.

5. The audio device of claim 1, wherein the processing unit is further configured to introduce at least one visual cue to alert the subject of the one or more sounds while the subject is wearing the audio device in the sleep environment, and further comprising:
a transceiver configured to wirelessly transmit a command to introduce the visual cue in the sleeping environment.

6. The audio device of claim 1, further comprising a transceiver configured to wirelessly detect the one or more sounds.

7. The audio device of claim 1, further comprising:
at least one biosensor configured to measure at least one biosignal parameter of the subject while the subject is wearing the wearable audio device and the speaker is outputting the adjusted masking sound, and
wherein the processing unit is further configured to:
determine the subject is sleeping based on the biosignal parameter; and
in response to determining the subject is sleeping, performing at least one of: further decreasing an intensity of the adjusted masking sound, introducing haptics, amplifying an intensity of the detected one or more sounds, or wirelessly transmitting, via a transceiver, a command to introduce a visual cue in the sleep environment in an effort to alert the subject of the one or more sounds.

8. The audio device of claim 1, further comprising:
a transceiver configured to wirelessly receive input from the subject indicating at least one of the one or more sounds.

9. The audio device of claim 1, wherein the one or more predetermined sound properties comprise noise over a predetermined decibel level.

10. The audio device of claim 1, wherein the one or more predetermined sound properties comprise noise over a predetermined decibel level within a predetermined frequency spectrum.

11. The audio device of claim 1, wherein the at least one alarm or detector distributed in a different one of the plurality of rooms than the one occupied by the at least one microphone is configured to detect a non-acoustic event.

12. A method for alerting a subject, comprising:
outputting a masking sound;
detecting one or more sounds in a plurality of rooms, wherein at least one of the plurality of rooms includes a microphone and a different one of the plurality of rooms includes at least one alarm or detector;
determining whether the detected sound exhibits one or more predetermined sound properties and satisfies criteria for a sound of importance upon processing the one or more sounds with a notch filter;
in response to determining that the detected sound exhibits the one or more predetermined sound properties and satisfies the criteria for the sound of importance upon processing the one or more sounds with the notch filter, adjusting the masking sound to alert the subject of the one or more detected sounds;
outputting the adjusted masking sound;
detecting a biosignal parameter of the subject while outputting the adjusted masking sound;
determining that the subject is sleeping based at least in part on the detected biosignal parameter, and in response to the determination, further adjusting the adjusted masking sound in a closed-loop manner to wake up the subject of the detected one or more sounds.

13. The method of claim 12, wherein adjusting the masking sound comprises at least one of:
reducing a sound pressure level of the masking sound or altering a frequency spectrum of the masking sound.

14. The method of claim 12, further comprising:
in response to determining the subject is sleeping, introducing at least one of a visual cue or haptic output in an effort to alert the subject of the detected one or more sounds;
monitoring the biosignal parameter of the subject while introducing the visual cue or haptic output;
determining the subject is not awake based on the monitored biosignal parameter; and
in response to determining the subject is not awake, continuing the visual cue or the haptic output.

15. The method of claim 14, further comprising:
determining the subject is awake based on the monitored biosignal parameter; and
in response to determining the subject is awake, stopping the visual cue or the haptic output.

16. The method of claim 12, further comprising:
in response to determining the subject is sleeping, gradually increasing a sound pressure level of the masking sound until the subject is determined to be awake.

17. The method of claim 16, wherein the subject is determined to be awake based on a determined biosignal parameter.

18. The method of claim 16, wherein the subject is determined to be awake based on input received from the subject.

19. The method of claim 12, wherein the one or more sounds comprise a combination of preconfigured safety alarms and sounds selected by the subject.

20. The method of claim 12, wherein at least one of the sounds selected by the subject comprises:
a sound recorded by the subject.

21. The method of claim 12, wherein detecting the one or more sounds in the vicinity of the subject comprises:
wirelessly receiving an indication of the detected one or more sounds.

22. A wearable audio device comprising:
a speaker configured to output a masking sound at a first sound pressure level (SPL);
at least one microphone configured to detect a noise greater than a threshold decibel value in a sleeping environment, the noise including a sound of importance identified using a notch filter, wherein the sleeping environment has a plurality of rooms and at least one of the plurality of rooms includes one of the at least one microphone and a different one of the plurality of rooms includes at least one alarm or detector operable to detect an event and, in response, provide an acoustic output exceeding the threshold decibel value to the at least one microphone and including the sound of importance identifiable using the notch filter;
a processing unit configured to receive signals from the at least one microphone in response to the detected noise, and to decrease the masking sound from the first SPL to a second SPL, in an effort to alert a subject of the detected noise while the subject is wearing the audio device in the sleeping environment,
wherein the speaker is further configured to output the masking sound at the second SPL;
a biosensor configured to detect a biosignal parameter of the subject while the subject is wearing the wearable audio device and the speaker is outputting the masking sound at the second SPL,
wherein the processing unit is configured to:
determine the subject is not awake based on the biosignal parameter; and
in response to the determination, wirelessly introduce a visual cue or a haptic output until the subject is determined to be awake based on a detected biosignal parameter.

23. The wearable audio device of claim 22, wherein the processing unit is further configured to amplify the detected noise in response to determining the subject is not awake.

\* \* \* \* \*